(12) United States Patent
Négrier et al.

(10) Patent No.: US 6,271,025 B1
(45) Date of Patent: Aug. 7, 2001

(54) MODIFIED FACTOR VIII CDNA

(75) Inventors: Claude Négrier, Irigny; Jean Luc Plantier, Grigny, both of (FR)

(73) Assignee: Aventis Behring GmbH, Marburg (DE)

( * ) Notice: Subject to any disclaimer, the term of this patent is extended or adjusted under 35 U.S.C. 154(b) by 0 days.

(21) Appl. No.: 09/526,935

(22) Filed: Mar. 16, 2000

(30) Foreign Application Priority Data

Mar. 17, 1999 (EP) .................................. 99104050

(51) Int. Cl.$^7$ .......................... C12N 15/00; C12N 15/63; C12P 21/06; C07H 21/04
(52) U.S. Cl. .................. 435/320.1; 435/69.1; 435/69.6; 435/455; 435/461; 435/325; 536/23.1; 536/23.5
(58) Field of Search .............................. 514/44; 536/23.1, 536/23.5; 435/69.1, 320.1, 455, 69.6, 461, 325

(56) References Cited

FOREIGN PATENT DOCUMENTS

| 2 763 959 | 12/1998 | (FR) . |
| WO 92/16557 | 10/1992 | (WO) . |
| WO 94/19471 | 12/1994 | (WO) . |

OTHER PUBLICATIONS

J. L. Plantier, et al., "A Combination of Truncated Factor IX Intron I Highly Improves FVIII Production," Blood, vol. 94, No. 10 Supp. 1 Part 1, p. 454a, Forty –first Annual Meeting of the American Society of Hematology. Abstract No. 2021, (1999).
Abstract, WO 98/55639 (Dec. 10, 1998).
Kozak, M. "Recognition of AUG and Alternative Initiator Codons is Augmented by G in Position +4 but is not Generally Affected by the Nucleotides in Positions +5 and +6," EMBO Journal, vol. 16, pp. 2482–2492 (1997).
Kurachi S., et al. "Role of Intron 1 in the Expression of the Human Factor IX Gene," Journal of Biological Chemistry, vol. 270, pp. 5276–5281 (1995).
Lind, P., et al., "Novel Forms of B–domain–deleted Recombinant Factor VIII Molecules. Construction and Biochemical Characterization", European Journal of Biochemsistry, vol. 232, pp. 19–27 (1995).
Lynch, C.M., et al. "Sequences in the Coding Region of Clotting Factor VIII Act as Dominant Inhibitors of RNA Accumulaton and Protein Production," Human Gene Therapy, vol. 4, pp. 259–272 (1993).
Nichols, W.C., et al. "Mutations in the Er–Golgi Intermediate Compartment Protein ERGIC–53 Cause Combined Deficiency of Coagulation Factors V and VIII," Cell, vol. 93, pp. 61–70 (1998).

Pipe, S.W., et al. "Differential Interaction of Coagulation Factor VIII and Factor V with Protein Chaperones Calnexin and Calreticulin," Journal of Biological Chemistry, vol. 273, pp. 8537–8544 (1998).
Pittman, D.D., et al. "Biochemical, Immunological, and In Vivo Function Characterization of B–domain–deleted Factor VIII," Blood, vol. 81, pp. 2925–2935 (1993).
Pittman, D.D., et al. "Role of the B–domain for Factor VIII and Factor V Expression and Function," Blood, vol. 84, pp. 4214–4225 (1994).
Vlot, A.J., et al. "Factor VIII and von Willebrand Factor," Thromb. Haemost., vol. 79, pp. 456–465 (1998).
Dorner, A.J., et al. "The Relationship of N–Linked Glycosylation and Heavy Chain–binding Protein Association with the Secretion of Glycoproteins," Journal of Cell Biology, vol. 105, pp. 2665–2674 (1987).
Fallaux, F.J., et al. "The Human Clotting Factor VIII cDNA Contains an Autonomously Replicating Sequence Consensus—and Matrix Attachment Region–like Sequence that Binds a Nuclear Factor, Represses Heterologuos Gene Expression, and Mediates the Transcriptional Effects of Sodium Butyrate," Mol. Cell. Biol., vol. 16, pp. 4264–4272 (1996).
Foster, P.A., et al. "Factor VIII Structure and Function," Blood Reviews, vol. 3, pp. 180–191 (1989).
Hoeben, R.C. et al. "Expression of the Blood–Clotting Factor–VIII cDNA is Repressed by a Transcriptional Silencer Located in its Coding Region," Blood, vol. 85, pp. 2447–2454 (1995).
Kaufman, R.J. "Biological regulation of Factor VIII Activity," Annual Reviews of Medicine, vol. 43, pp. 325–339 (1992).
Kaufman, R.J., et al. "Effects of von Willebrand Factor Coexpression on the Synthesis and Secretion of Factor VIII in Chinese Hamster Ovary Cells," Mol. Cell. Biol., vol. 9, pp. 1233–1242 (1989).
Koeberl, D.D., et al. "Sequence within the Coding Regions of Clotting Factor VIII and CFTR Block Transcriptional Elongation," Human Gene Therapy, vol. 6, pp. 469–479 (1995).

Primary Examiner—Karen M. Hauda
Assistant Examiner—Quang Nguyen
(74) Attorney, Agent, or Firm—Finnegan, Henderson, Farabow, Garrett and Dunner, L.L.P.

(57) ABSTRACT

A modified Factor VIII cDNA is described comprising deletion of the B-domain and insertion of at least one truncated Factor IX intron 1 in the Factor VIII cDNA. The modified Factor VIII cDNA may be used for the production of a high yield of Factor VIII in vitro. The modified Factor VIII cDNA may be incorporated into a vector for gene therapy.

6 Claims, 5 Drawing Sheets

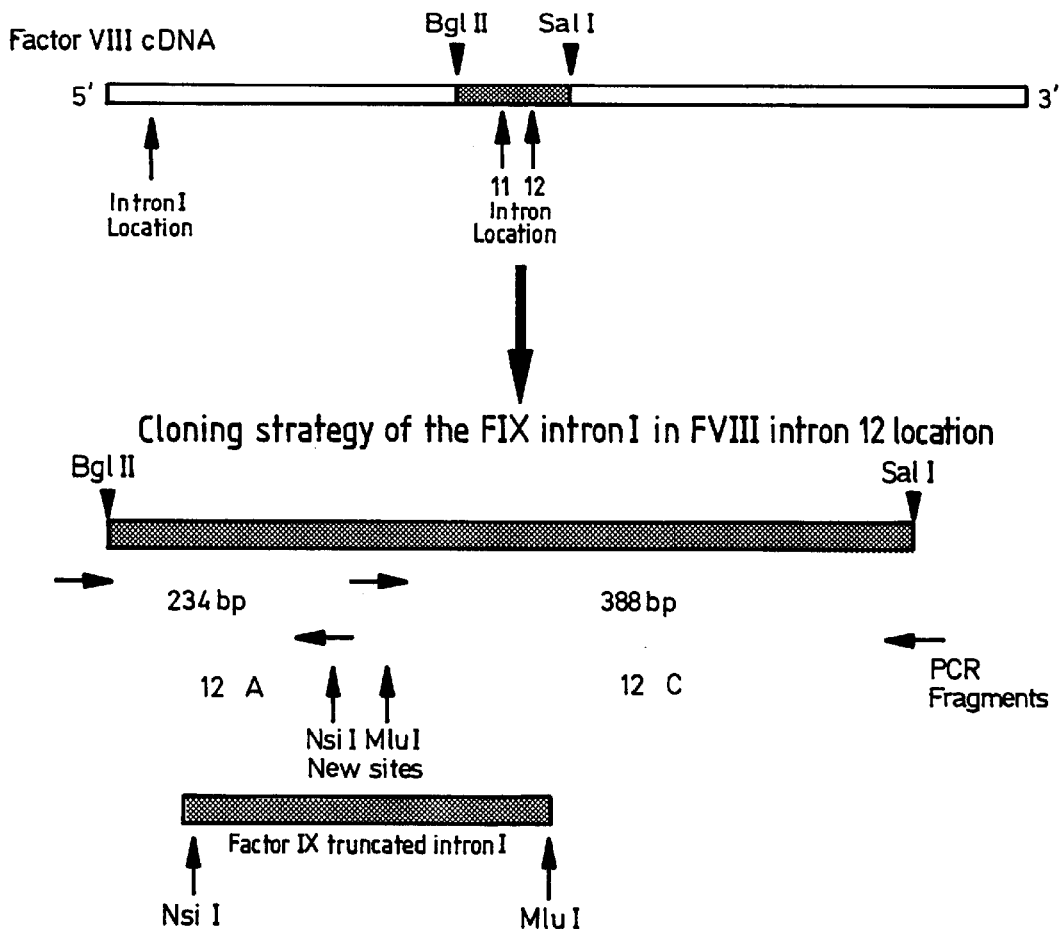
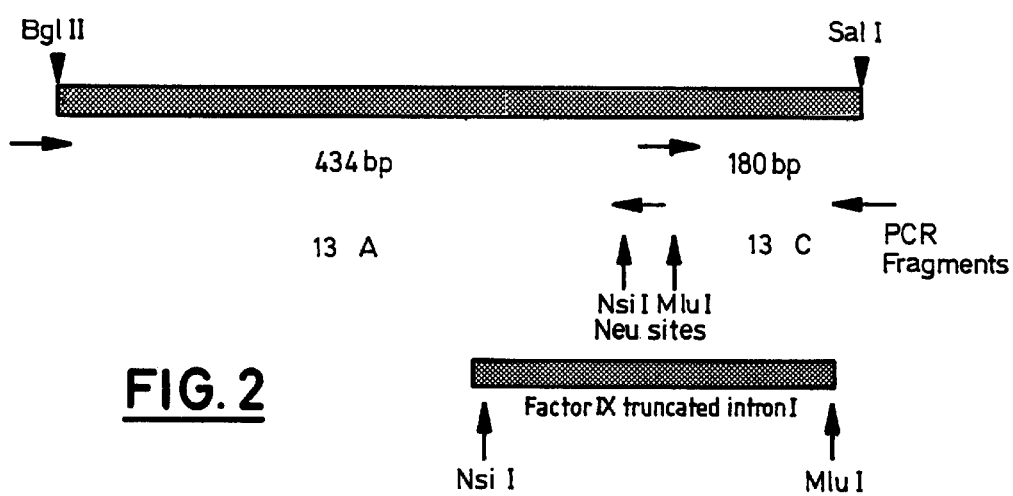
FIG. 2

Kinetic of FVIII production from different transfected cell lines

Procoagulant activities from different transfected cell supernatants

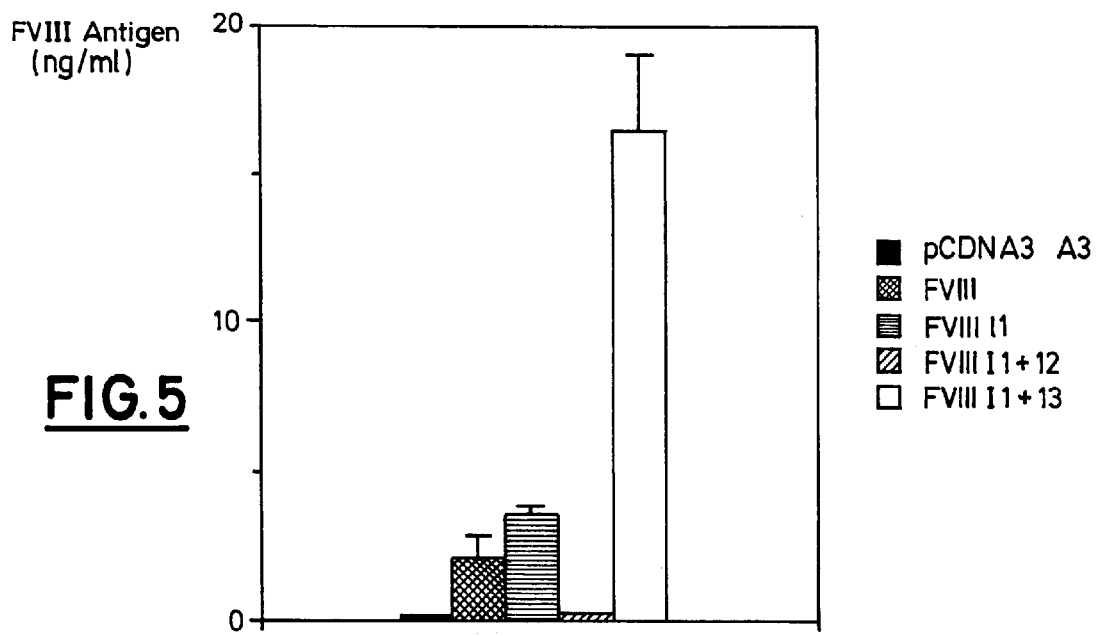
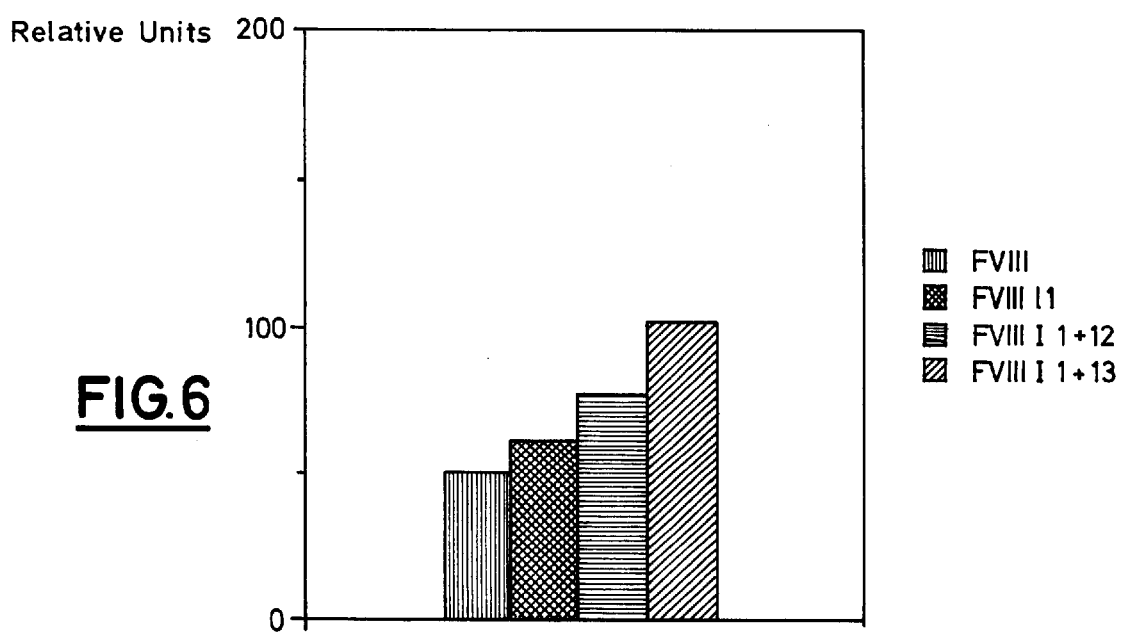

MODIFIED FACTOR VIII CDNA

This invention is directed to a modified Factor VIII cDNA and its use for the improvement of the Factor VIII production.

Factor VIII (FVIII) is a plasma coagulation cofactor implicated in the activation of Factor X (FX). A decrease in the presence or activity of Factor VIII in blood stream leads to hemophilia A. The level of the decrease in Factor VIII activity is directly proportional to the severity of the disease (Foster and T. S., 1989; Kaufman, 1992; Vlot et al., 1998). The current treatment of hemophilia A consists of the replacement of the missing protein by plasma-derived or recombinant FVIII. Recombinant FVIII is produced in CHO or BHK cells after selection of the best producing clones and amplification of the FVIII cDNA copy number.

Several studies have stressed the low FVIII production level in different cellular systems: Biosynthesis of FVIII was shown to be regulated in at least three different levels. First, among the FVIII cDNA sequence two nucleotides stretches, localized in the A2 coding domain, were demonstrated to act as transcriptional silencers (Fallaux et al, 1996; Hoeben et al., 1995; Koeberl et al., 1995; Lynch et al., 1993). Second, FVIII protein synthesis is tightly regulated by several reticulum endoplasmic chaperones (BiP; Calreticulin; Calnexin; ERGIC-53). Many of these interactions retain FVIII in the cell and direct it through the cellular degradation machinery (Dorner et al., 1987; Nichols et al., 1998; Pipe et al., 1998). Third, once secreted FVIII is sensitive to protease degradation and needs to be protected by von Willebrand Factor (vWF) (Kaufman et al., 1989).

It is therefore a problem to develop improved processes which result in higher yields of FVIII. The present invention offers a solution to this problem by a modified FVIII cDNA.

SUMMARY OF THE INVENTION

According to this invention, a modified FVIII cDNA is available comprising a truncated FIX intron 1 inserted in at least one location of the FVIII cDNA, in which the B-domain of the wild-type FVIII cDNA has been deleted. In addition, the B-domain of the wild-type cDNA has been replaced by four arginines.

BRIEF DESCRIPTION OF THE FIGURES

FIG. 2. Cloning strategy of Factor IX intron 1 in Factor VIII introns 12 and 13 locations.

FIG. 5. Factor VIII antigen production in a Hep G2 cell line.

FIG. 6. Quantitative analysis of Factor VIII mRNA in transfected Chinese Hamster Ovary cells.

DETAILED DESCRIPTION

Figure 1:
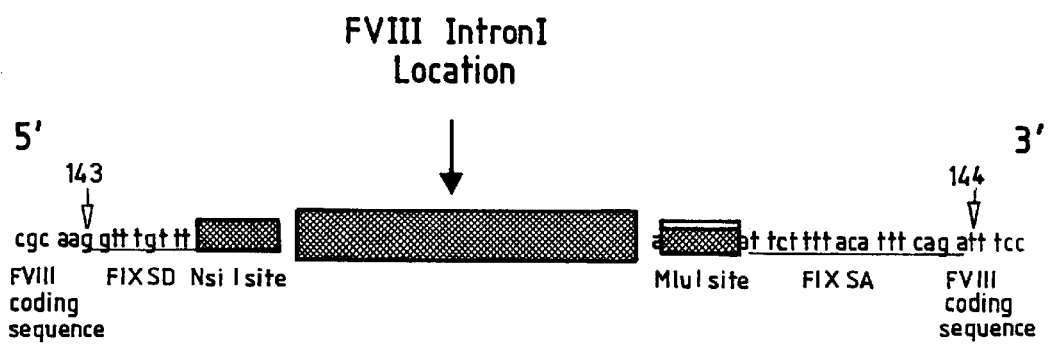
FIG. 1. Schematic view of the Factor IX intron 1 inserted in the Factor VIII intron 1 location.

The FVIII constructs were prepared as follows:

1. FVIII CLONING

A PCR cloning strategy was designed, based on the synthesis of four PCR fragments spanning the FVIII cDNA, except for the B-domain. Based on published data, it was of interest to replace the B-domain with four arginines. Using the MoMuLV reverse transcriptase (Promega, Charbonnieres, France), a reverse transcription was done on human cell RNA isolated from a liver biopsy with the written consent of the patient. Four PCR fragments were generated using the Expand System (Beoringer-Mannheim, Germany) as described in Table 1.

TABLE I

Summary of FVIII PCR fragments

| Fragment | Oligonucleotide Sense antisense | SEQ ID No. | Size in bp | 5' cloning site | 3' cloning site |
|---|---|---|---|---|---|
| 1 | FVIII ATG<br>3'Bgl II | No.1<br>No.2 | 1704 | Not I | Bgl II |
| 2 | 5'Bgl II<br>4R AS | No.3<br>No.4 | 624 | Bgl II | Sal I |
| 3 | 4R S<br>3'Bgl I | No.5<br>No.6 | 1093 | Sal I | Bgl I |
| 4 | 5'Bgl I<br>FVIII stop | No.7<br>No.8 | 1026 | Bgl I | Xho I |

All the oligonucleotide sequences used for cloning are shown in Annex 1.

An additional improvement was performed by optimisation of the ATG environment following the rules of Kozak (Kozak, 1997). For this purpose the oligonucleotide FVIII ATG (SEQ ID No 1) was used.

Comparison of the Wild-type FVIII ATG and the Kozak Modified FVIII ATG Sequences WT sequence: TAA GTC ATG CAA ATA (SEQ. ID No. 10)

Kozak modified: ACA CCC ATG GAA ATA (SEQ. ID No. 11)

The modified amino acids are represented in bold.

Four arginines replace, according to the invention, the B-domain of the FVIII protein. They are introduced by the oligonucleotides used for the cloning of the two fragments surrounding the B-domain (see Fragments 2 and 3 of Table I), namely the oligonucleotides 4R AS (SEQ.ID.No.4) and 4R S (SEQ.ID.No.5). The Sal I site was generated by the coding sequence of the arginines as follows:

SAL I SITE

4R S:5'-A AGA CGT CGA CGA TAA ATA ACT CGT ACT ACT CTT(SEQ ID. NO. 5)

4R AS TTG TTA CGG TAA CTT GGT TCT TCT GCA GCT GCT CTT (SEQ ID No. 4)

CORRESPONDING PEPTIDIC SEQUENCE

Pro Arg Arg Arg Arg Glu Ile Thr Arg Thr Thr Leu (SEQ ID No. 12)

In the wild-type FVIII the peptidic sequence is:

Pro-Arg-Domain B-Arg-Glu (SEQ ID No. 13).

This indicates that a Sal I restriction site was inserted through the middle of the fourth arginine coding sequence without any sequence alteration. All PCR fragments were cloned in a pCR2 vector using the T/A cloning kit (InVitrogen, the Netherlands). Two clones of each fragment were entirely sequenced. Some mutations were found in a ratio of 1 for 800 bases. One mutation was silent but three others modified the coding sequence and the three cDNA pieces bearing the mutations were successively exchanged.

A subsequent sub-cloning strategy leads to the production of two fragments (each being the sum of two PCR products): a 5' 2.3 kb (FVIII ATG) and a 3' 2.1 kb (FVIII Stop). The 5' 2.3 kb (FVIII ATG) and a 3' 2.1 kb (FVIII Stop) were constructed and inserted in the expression vector pCDNA3 (InVitrogen, The Netherlands) opened by Not I and Xho I and treated with alkaline phosphatase. The cloning cassette of pCDNA3 presents a similar restriction sequence as pCR2 and the vector possesses its own resistance gene (neomycin). A B-domain deleted FVIII coding cDNA (hereafter refered to Factor VIII cDNA) was directly obtained in the expression vector. The final FVIII cDNA integrity was checked by extensive restriction analysis.

Factor VIII cDNA was subcloned in the Bluescript pKS II+vector opened by Not I and Xho I. The use of this vector was more convenient for the introduction of subsequent modifications in Factor VIII cDNA (e.g. introns addition; see hereafter).

2. TRUNCATED FIX INTRON 1 INSERTION

According to the invention the FVIII cDNA was further modified by the insertion of a Factor IX truncated intron 1 (FIX TI1=SEQ.ID.No.9). The FIXTI1 was inserted in different locations of the FVIII cDNA as follows:

- in the FVIII intron 1 location, to use a similar strategy as for FIX (Kurachi et al., 1995)
- in the FVIII intron 12 and 13 locations, because a transcriptional silencer sequence was described in this region.
- in the FVIII introns 1+12 and 1+13 locations. Since FVIII cDNA is much larger than FIX (4.4 kb vs 1.4 kb), we hypothesized that it might be of interest to introduce supposedly stabilizing sequences at the locations normally occupied by introns 12 and 13 in addition to intron 1. Since the location of introns 12 and 13 are grossly in the middle of the FVIII sequence it is possible that they may act synergistically with intron 1.

The FIXTI1-Sequence (=SEQ-ID No. 9)used according to the invention in different locations of the FVIII cDNA starts after the coding sequence by the splice donor sequence and ends by the splice acceptor sequence of the truncated intron 1. The upper case letters start after and stop before the Nsi I and Mlu I restriction sites, respectively. For details see Annex 2.

For cloning this fragment in an exogenous sequence, two new FVIII junction fragments were generated, one upstream the FIX TI1 with the addition of a Nsi I site and one downstream with the addition of a Mlu I site. The three fragments were subsequently linked together using these sites.

A similar strategy was used for inserting the three FIXTI1 in different locations. In each case three PCR fragments (A, B, C) were generated with the Expand System using Factor VIII cDNA as template for segments A and C, and Factor IX intron 1 for the B fragment. The A fragment extremities comprise Factor VIII sequence on the 5' end, and on the 3' end a fusion between the FVIII 3' splicing sequence and the Factor IX first intron 5' splicing sequence. A Nsi I restriction site was added between these two sequences. The B fragment possesses at the 5' extremity a complementary sequence to the previous fragment, the truncated Factor IX intron 1, and at the 3' end an inserted MluI restriction site. The C fragment was made of the complementary sequence of the 3' extremity from fragment B followed by the Factor IX first intron 3' splicing sequence and by the Factor VIII cDNA downstream coding sequence (see FIG. 1).

The B fragment was the same for all constructs whereas A and C were all different, corresponding to the 5' and 3' FVIII sequences of the intron insertion sites.

The insertion strategies for intron 12 and 13 positions are indicated in FIG. 2.

Each PCR fragment was generated and first cloned in pCR2 vector using TIA cloning kit (InVitrogen, The Netherlands). They were linked together in two successive steps (pCR2-B+C/MluI+XhoI; pCR2-A+BC/NsiI+XbaI). All ABC (1, 12 and 13) fragments were sequenced and shown to be free of mutations.

TABLE II

Summary of the PCR fragments required for introducing TFIXI1.

| Fragment Name | Size in bp |
|---|---|
| I1-A | 204 |
| TFIXI1 (B) | 281 |
| I1-C | 464 |
| I12-A | 234 |
| I12-C | 388 |
| I13-A | 434 |
| I13-C | 180 |

ABC1 was cloned in pKS II+FVIII after Spe I-Spe I digestion. After checking the orientation, the resulting FVIII I1 cDNA was subcloned in pCDNA3 vector using a Not I-Xho I digestion. ABC12 and ABC13 were digested by Bgl II and Sal I and ligated in pKSII-FVIII digested by the same enzymes. Resulting FVIII I12 and FVIII I13 were subcloned in pCDNA3 using a Not I-Xho I restriction.

To generate a construct containing two introns, pKS FVIII I1 and the fragments ABC 12 or ABC 13 were digested by Bgl II and Sal I and ligated together. pKSII FVIII I1+12 and FVIII I1+13 were obtained and FVIII cDNAs containing the introns were subcloned in pCDNA3 by the same strategy as previously described.

3. GENERATION OF STABLY EXPRESSING FVIII CELL LINES

All pCDNA3-FVIII constructs were transfected in CHO cells by electroporation. Briefly, $7\times10^6$ washed CHO cells were electroporated in the presence of 10 g of Pvu I linearized construct. The cells were selected 15 hours after electroporation in IMDM (=Iscove's Modified Dulbecco's Medium) supplemented by antibiotics and 10% fetal calf serum containing 0.6 mg/ml G418. For each construct (FVIII; I1, I12; I13; I1+12; I1+13), two pools of clones containing more than 50 individual colonies were grown and frozen. A set of 25 individual colonies were picked up, grown and assessed for Factor VIII expression using an ELISA method (Asserachrom VIIIC.Ag, Diagnostica STAGO, Asnieres, France). For all clones, the transfection efficiency was around 40–60% as determined by the number of expressing clones. The five best FVIII producer clones were kept and frozen. The FVIII antigen detected varied dramatically from one construct to another.

The activity of the recombinant Factor VIII was measured using the classical one stage clotting assay for each pool and five selected clones. A coagulant activity was found in each supernatant of Factor VIII expressing cells indicating that the construct was coding for a functional protein. The activity was correlated to the amount of protein detected by ELISA. Therefore, it was demonstrated that each construct allowed the production of a functional procoagulant FVIII.

4. EVALUATION OF THE CONSTRUCT EFFICIENCY

4.1 Quantitative Analysis in CHO Cells

Figure 3:
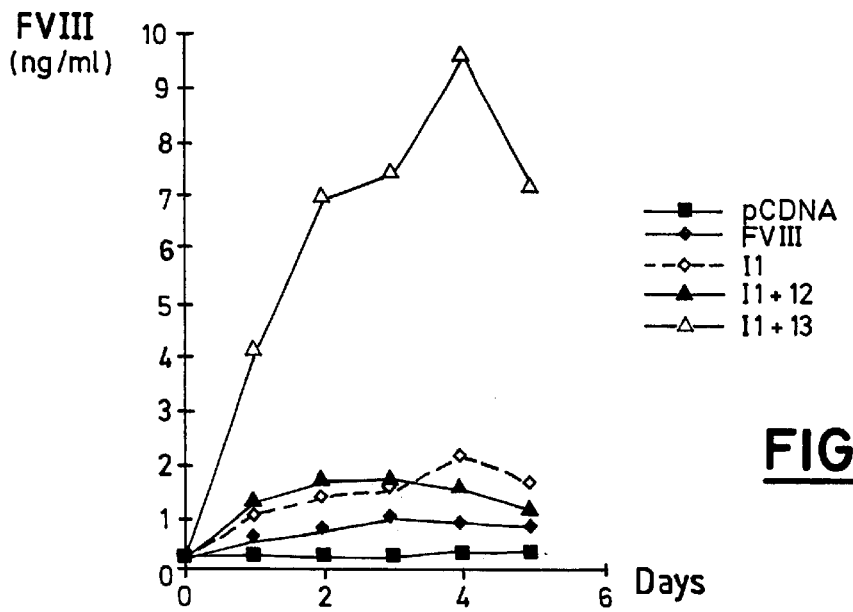
FIG. 3. Kinetic of Factor VIII production from different transfected cell lines.
Figure 4:
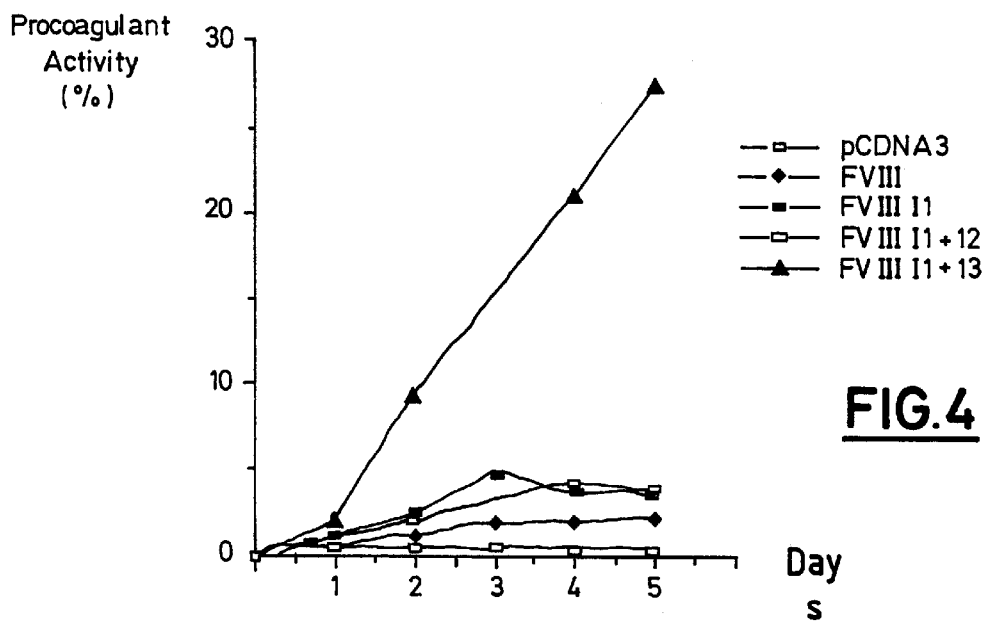
FIG. 4. Procoagulant activities from different transfected cell supernatants.

The kinetic of FVIII production was analyzed for each pool of transfected CHO cells. For each pool, independent experiments were made by two different experimenters. At day 0.4×10⁵ cells were seeded in a 6-well plate in 2 ml of fresh medium containing 0.6 mg/ml G418. From day 1 to day 4, the culture supernatant was collected, centrifuged and assayed for FVIII antigen and procoagulant activity. Each day, after medium removal, cells were trypsinized and counted in Trypan Blue. FVIII accumulation is shown in FIG. 3. Three constructs allowed a better production than the non-modified FVIII cDNA, i.e. FVIII I1, FVIII I1+12 and particularly FVIII I1+13. FVIII I1 and FVIII I1+12 led to a 2 to 3 times higher production and FVIII I1+13 to 8 to 9 times more. Procoagulant activities were measured from the same supernatants and are presented in FIG. 4. They were directly correlated to the amount of antigen detected.

4.2 Quantitative Analysis in HepG2 Cells

To confirm the data obtained in CHO cells, a second cellular model was chosen. The constructs exhibiting an improvement in the FVIII expression were tested (e.g. FVIII; FVIII I1, FVIII I1+12; FVIII I1+13) using transiently transfected hepatic cell line HepG2.2 g of circular DNA were added to 12 I of Fugene 6 transfection reagent (Boehringer Mannheim, Meylan, France). After 15 minutes, the complex was added dropwise on a 90 mm dish seeded with 5×10⁶ cells the day before. The transfection mix was incubated for 6 h before being replaced by 4 ml of fresh medium. Culture medium was collected 72 h later and submitted to coagulation and ELISA assays. As shown in FIG. 5, the results obtained using HepG2 cells confirmed the data obtained in CHO cells with the exception of FVIII I1+12 construct which here did not product any detectable FVIII antigen. These data reinforced the potential interest in the FVIII I1+13 construct.

5. ANALYSIS OF THE EXPRESSION LEVELS

Total RNA of each transfected pool A was extracted with the Rneasy mini Kit (Quiagen), 6.10⁶ cells being used for each extraction. 10 g of total RNA were migrated at 120V, 4 C in a 0.8% agarose gel in phosphate buffer, transferred overnight on Hybond-N Nylon membrane (Amersham) and baked for 2 h at 80 C. A FVIII RNA probe, containing the 1.03 kb Sal I-Bgl I fragment, was generated by T7 polymerase using the RNA DIG labelling kit (Boehringer). The membrane was blocked 30 min by the Dig easy Hyb solution (Boehringer) and incubated in the same fresh solution overnight with 500 ng of labeled antisense probe. Washes were conducted as recommended by the manufacturer and the blot was revealed using the DIG detection Kit (Boehringer) analysed and quantified. FVIII signals were compared to ribosomal BET-labeled RNA and to GAPDH signal.

FVIII, FVIII I1 and FVIII I+12 mRNA amounts were very close to each other. FVIII I1+13 mRNA was expressed in larger amounts. These results indicate a correlation between the amount of mRNA and the protein produced for the constructs (see FIG. 6).

A two time increase in FVIII I1+13 mRNA lead to a 8 to 9 times protein increase. Therefore, the addition of truncated FIX intron I might play a double role in stabilizing FVIII mRNA but also probably in acting during translation.

The mRNA from FVIII is 4.4 kb long and the differences of 0.3 kb due to a possible non splicing of the TFIXI1 may not be visible in Northern blot. A RT-PCR set of experiments was done on total RNA extracted from the different cell lines. In each case a band corresponding to a spliced mRNA was obtained indicating the splicing of the TFIXI1 from FVIII mRNA.

6. PROTEIN CHARACTERIZATION

A sheep anti-FVIII antibody from Cedarlane (Homby, Canada) was purchased and positively tested in a control immunoblot using recombinant FVIII. This antibody was used in immunoblot on cell supernatant but no signal was obtained due to the low amount of secreted antigen. An immunoprecipitation was done on cell supernatant but here again no signal was obtained indicating the inability of this antibody to immunoprecipitate FVIII. An immunoblot was done o Triton-X100 soluble cell lysates. 90 mm dishes was lysed with 300 I ice-cold lysis buffer (Hepes 20 mM pH7.5, KCl 100 mM, $MgCl_2$ 2 mM, Triton X-100 0.5%). Cells were scrapped and centrifuged at 4 C, 10 min at 14000 g. Protein concentration was measured with the Dc-protein Assay kit (BioRad, Hercules, USA). 175 g of each cell lysates were loaded on 7.5% acrylamide gel and treated following the Laemmli protocol. After semy-dry transfer (35 min at 400 mA), the nitrocellulose membrane was incubated overnight in TBS-T (20 mM Tris pH 7.5, NaCl 0.15 M, Tween-20 0.5%). The membrane was then incubated 1 h with the anti-FVIII antibody (5 g/ml) in TBS-T. After three washes of 10 min each in TBS-T, the membrane was incubated for 30 min with a rabbit anti-sheep peroxidase coupled antibody (dilution $10^{-4}$ in TBS-T). Extensive washes were conducted before revelation with the ECL system (Amersham).

Among all the lysates, only the cells transfected with the FVIII I1+13 construct gave a positive signal with a correct approximative molecular weight. The FVIII I1+13 appeared as a single band product migrating at a molecular weight corresponding to the Factor VIII heavy chain devoided of the B-domain.

Figure 7:
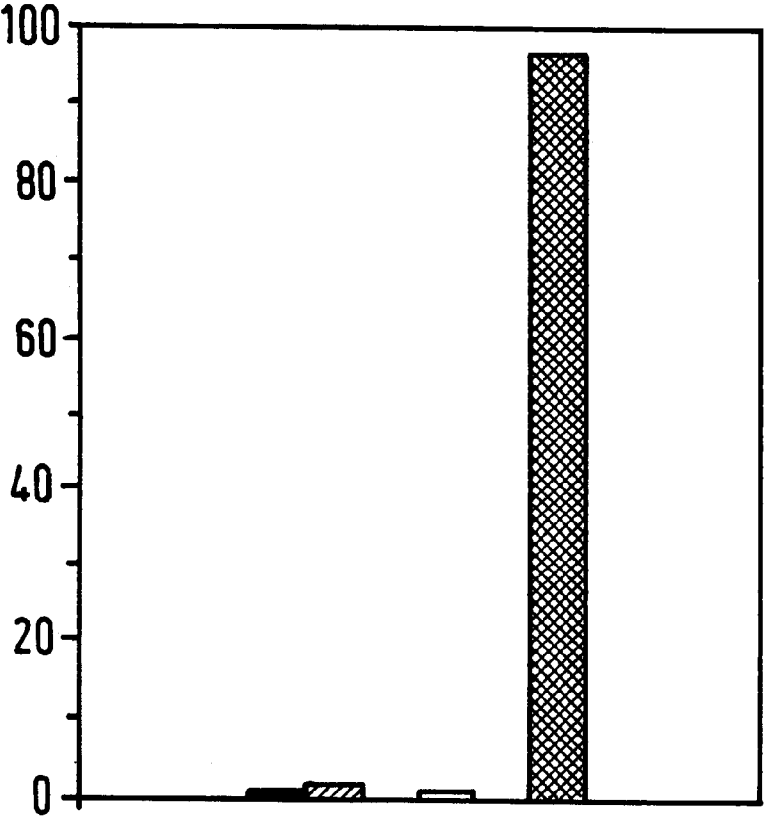
FIG. 7. Intracellular amount of Factor VIII in different cell lines.

In order to confirm the differences observed in intracellular FVIII amounts, an ELISA was done on Triton-X 100 soluble lysates. The presence of Triton X-100 was shown not to influence the FVIII ELISA test. The value of FVIII antigen present inside the cells confirms the data obtained in Western blot. FVIII I1+13 led to a 100 times higher synthesis of the antigen than all other constructs (29 ng/ml vs. 0.3 ng/ml for FVIII) (see FIG. 7).

Subject of the invention are, therefore, FVIII-B-domain deleted constructs containing a slightyl modified Factor IX truncated intron I in different locations of the cDNA. Among these constructs a cDNA bearing the truncated intron I in both the FVIII Intron 1 and Intron 12 locations led to a 100 times higher intracellular production than all other constructs and a 9 times higher secretion of the protein. This improved production and secretion was observed in two different cell lines: CHO and HepG2 cells. The FVIII produced was fully active on a one stage clotting assay and appears homogenous on immunoblot. The mRNA amount of all the constructs tested differs no more than three times indicating that the benefit observed in the production is coming both from a transcriptional and a translational effect.

The present invention indicates that the production of FVIII may be improved by adding introns in the FVIII cDNA. The advantages of such modified FVIII cDNAs for in vitro FVIII production as well as for human gene therapy by inserting such a cDNA in a suitable transfervector are important for the future treatment of hemophilia A.

BIBLIOGRAPHY

Dorner, A. J., Bole, D. G., and Kaufman, R. J. (1987): The relationship of N-Linked Glycosylation and Heavy Chain-binding Protein Association with the Secretion of Glycoproteins. *J. Cell, Biol.* 105, 2665–2674.

Fallaux, F. J., Hoeben, R. C., Cramer, S. J., van den Wollenberg, D. J., Briet, E., van Ormondt, H., and van der Eb, A. J. (1996): The human clotting factor VIII cDNA contains an autonomously replicating sequence consensus- and matrix attachment region-like sequence that binds a nuclear factor, represses heterologuos gene expression, and mediates the transcriptional effects of sodium butyrate. *Mol Cell Biol* 16, 4264–72.

Foster, P. A., and T. S., Z. (1989): Factor VIII structure and Function. *Blood Reviews* 3, 180–191.

Hoeben, R. C., Fallaux, F. J., Cramer, S. J., van den Wollenberg, D. J., van Ormondt, HI, Briet, E., and van der Eb, A. J. (1995): Expression of the blood-clotting factor-VIII cDNA is repressed by a transcriptional silencer located in its coding region. *Blood* 85, 2447–54.

Kaufman, R. J. (1992): Biological regulation of factor VIII activity. *Annu Rev Med* 43, 325–39.

Kaufman, R. J., Wasley, L. C., Davies, M. V., Wise, R. J., Israel, D. I., and Dorner, A. j. (1989): Effects of von Willebrand Factor Coexpression on the Synthesis and Secretion of Factor VIII in Chinese Hamster Ovary Cells. *Mol. Cell. BIol.* 9,1233–1242.

Koeberl, D. D., Halbert, C. L., Krumm, A., and Miller, A. D. (1995): Sequences within the coding regions of clotting factor VIII and CFTR block transcriptional elongation. *Hum Gene Ther* 6, 469–79.

Kozak, M. (1997: Recognition of AUG and alternative initiator codons is augmented by G in position +4 but is not generally affected by the nucleotides in positions +5 and +6. *EMBO J.* 16, 2482–92.

Kurachi S., Hitomi Y., Furukawa M., and Kurachi K. (1995). Role of the Intron 1 in the expression of the human Factor IX gene. J. Biol. Chem. 270, 5276–5281.

Lind, P., Larsson, KI, Spira, J., Spira, J., Sysow Backman, M., Almstedt, A., Gray, E., and Sandberg, H. (1995): Novel forms of B-domain-deleted recombinant factor VIII molecules. Construction and biochemical characterization. *Eur J Biochem* 232, 19–27.

Lynch, C. M., Israel, D. I., Kaufman, R. J., and Miller, A. D. (1993): Sequences in the coding region of clotting factor VIII act as dominant inhibitors of RNA accumulaton and protein production. *Hum Gene Ther* 4, 259–72.

Nichols, W. C., Seligsohn, U., Zivellin, A., Terry, V. H., Hertel, C. E., Wheatley, M. A., Moussali, M. J., Hauri, H.-P., Ciavarella, NI, Kaufman, R. J., and Ginsburg, D. (1998): Mutations in the ER-Golgi Intermediate Compartment Protein ERGIC-53 Cause Combined Deficiency of Coagulation Factors V and VIII. *Cell* 93, 61–70.

Pipe, S. W., Morris, J. A., Shah, JI, and; Kaufman, R. J. (1998): Differential Interaction of Coagulation Factor VIII and Factor V with Protein Chaperones Calnexin and Calreticulin. *J. Biol. Chem.* 273, 8567–8544.

Pittman D. D., Alerman, E. M., Tomkinson, K. N., Wang, J. H., Giles, A. R., and Kaufman, R. J. (1993: Biochemical, immunological, and in vivo functional characterizaton of B-domain-deleted factor VIII. *Blood* 81, 2925–35.

Pittman, D. D., Marquette, K. A., and Kaufman, R. J. (1994): Role of the B-domain for factor VIII and factor V expression and function. *Blood* 84, 4214–25.

Vlot, A. J., Koppelman, S. J., Bouma, B. N., and Sixma, J. J. (1998): Factor VIII and von Willebrand Factor. *Thromb. Haemo.* 79, 456–465.

What is claimed is:

1. A modified Factor VIII cDNA comprising a deletion of the B-domain and insertion of the truncated Factor IX intron 1 (SEQ ID NO: 9) in one or more splice sites of the Factor VIII cDNA, wherein said cDNA encodes a polypeptide having Factor VIII activity.

2. A modified Factor VIII cDNA comprising a replacement of the B-domain with nucleotides encoding four arginines and insertion of the truncated Factor IX intron 1 (SEQ ID NO: 9) in one or more splice sites of the Factor VIII cDNA, wherein said cDNA encodes a polypeptide having Factor VIII activity.

3. The modified Factor VIII cDNA as claimed in claim 1, wherein at least one insertion site of the truncated Factor IX intron 1 is chosen from Factor VIII intron 1 splice site, Factor VIII intron 12 splice site, and Factor VIII intron 13 splice site.

4. The modified Factor VIII cDNA as claimed in claim 2, wherein at least one insertion site of the truncated Factor IX intron 1 is chosen from Factor VIII intron 1 splice site, Factor VIII intron 12 splice site, and Factor VIII intron 13 splice site.

5. A vector comprising the modified Factor VIII cDNA of claim 1.

6. A vector comprising the modified Factor VIII cDNA of claim 2.

* * * * *

SEQUENCE LISTING

```
<160> NUMBER OF SEQ ID NOS:  22

<210> SEQ ID NO 1
<211> LENGTH: 30
<212> TYPE: DNA
<213> ORGANISM: Homo sapiens

<400> SEQUENCE: 1
acacccatgg aaatagagct ctccacctgc                                          30

<210> SEQ ID NO 2
<211> LENGTH: 24
<212> TYPE: DNA
<213> ORGANISM: Homo sapiens

<400> SEQUENCE: 2
agtcctgaag ctagatctct ctcc                                                24

<210> SEQ ID NO 3
<211> LENGTH: 26
<212> TYPE: DNA
<213> ORGANISM: Homo sapiens

<400> SEQUENCE: 3
aatatggaga gagatctagc ttcagg                                              26

<210> SEQ ID NO 4
<211> LENGTH: 36
<212> TYPE: DNA
<213> ORGANISM: Homo sapiens
```

-continued

```
<210> SEQ ID NO 4
<211> LENGTH: 36
<212> TYPE: DNA
<213> ORGANISM: Homo sapiens

<400> SEQUENCE: 4
ttctcgtcga cgtcttcttg gttcaatggc attgtt                                36

<210> SEQ ID NO 5
<211> LENGTH: 34
<212> TYPE: DNA
<213> ORGANISM: Homo sapiens

<400> SEQUENCE: 5
aagacgtcga cgagaaataa ctcgtactac tctt                                  34

<210> SEQ ID NO 6
<211> LENGTH: 26
<212> TYPE: DNA
<213> ORGANISM: Homo sapiens

<400> SEQUENCE: 6
agcatgtaga tgctcgccaa taaggc                                           26

<210> SEQ ID NO 7
<211> LENGTH: 28
<212> TYPE: DNA
<213> ORGANISM: Homo sapiens

<400> SEQUENCE: 7
atttggcggg tggaatgcct tattggcg                                         28

<210> SEQ ID NO 8
<211> LENGTH: 33
<212> TYPE: DNA
<213> ORGANISM: Homo sapiens

<400> SEQUENCE: 8
acacctcgag tcagtagagg tcctgtgcct cgc                                   33

<210> SEQ ID NO 9
<211> LENGTH: 312
<212> TYPE: DNA
<213> ORGANISM: Homo sapiens

<400> SEQUENCE: 9
gtttgtttat gcatcctttt ttaaaataca ttgagtatgc ttgccttta gatatagaaa       60 tatctgatgc tgtcttcttc actaaatttt gattacatga tttgacagca atattgaaga      120
gtctaacagc cagcacgcag gttggtaagt actgtgggaa catcacagat tttggctcca     180
tgccctaaag agaaattggc tttcagatta tttggattaa aaacaaagac tttcttaaga     240
gatgtaaaat tttcatgatg ttttcttttt tgctaaaact aaagaattaa cgcgtattct     300
tttacatttc ag                                                         312

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
taagtcatgc aaata                                                       15
```

```
<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
acacccatgg aaata                                                          15

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Pro Arg Arg Arg Arg Glu Ile Thr Arg Thr Thr Leu
 1               5                  10

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<223> OTHER INFORMATION: "Domain B" insert between residues 2 and 3

<400> SEQUENCE: 13

Pro Arg Arg Glu
 1

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
catgcatcct tttttaaaat acattgag                                            28

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aacgcgttaa ttctttagtt ttagca                                              26

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aatgcataaa caaaccttgc gtccacaggc agctc                                    35
```

```
<210> SEQ ID NO 17
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aacgcgtatt cttttacatt tcagatttcc tcctagagtg cc                          42

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ttctctacat actagtaggg c                                                 21

<210> SEQ ID NO 19
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
aatgcataaa caaactgtgc atgatgttgg aggct                                  35

<210> SEQ ID NO 20
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aacgcgtatt cttttacatt tcaggcatca atggctatgt tt                          42

<210> SEQ ID NO 21
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aatgcataaa caaacctggg ttttccatcg acatgaa                                37

<210> SEQ ID NO 22
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aacgcgtatt cttttacatt tcaggtctat ggattctggg gt                          42
```